US010675311B2

(12) United States Patent
Tategaki et al.

(10) Patent No.: US 10,675,311 B2
(45) Date of Patent: Jun. 9, 2020

(54) LACTIC ACID BACTERIUM

(71) Applicant: KANEKA CORPORATION, Osaka-shi (JP)

(72) Inventors: Airo Tategaki, Takasago (JP); Taizo Kawabe, Takasago (JP); Hozumi Tanaka, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 15/204,641

(22) Filed: Jul. 7, 2016

(65) Prior Publication Data

US 2017/0232046 A1    Aug. 17, 2017

Related U.S. Application Data

(60) Division of application No. 14/611,739, filed on Feb. 2, 2015, now abandoned, which is a continuation-in-part of application No. PCT/JP2013/070286, filed on Jul. 26, 2013.

(30) Foreign Application Priority Data

Jul. 31, 2012    (JP) .............................. 2012-170136

(51) Int. Cl.
| | | |
|---|---|---|
| *A61K 35/744* | (2015.01) |
| *A23L 29/00* | (2016.01) |
| *A23K 10/18* | (2016.01) |
| *C12R 1/46* | (2006.01) |
| *A61K 9/00* | (2006.01) |
| *A61K 9/16* | (2006.01) |
| *A61K 9/19* | (2006.01) |
| *C12N 1/20* | (2006.01) |
| *A61K 35/74* | (2015.01) |
| *A61K 35/00* | (2006.01) |
| *A21D 8/04* | (2006.01) |
| *A23L 33/135* | (2016.01) |
| *C12N 15/74* | (2006.01) |

(52) U.S. Cl.
CPC ............ *A61K 35/744* (2013.01); *A21D 8/045* (2013.01); *A23K 10/18* (2016.05); *A23L 29/065* (2016.08); *A23L 33/135* (2016.08); *A61K 9/0056* (2013.01); *A61K 9/1617* (2013.01); *A61K 9/1623* (2013.01); *A61K 9/19* (2013.01); *C12N 1/20* (2013.01); *C12N 15/746* (2013.01); *C12R 1/46* (2013.01); *A23V 2002/00* (2013.01); *A61K 35/74* (2013.01); *A61K 2035/11* (2013.01)

(58) Field of Classification Search
None
See application file for complete search history.

(56) References Cited

U.S. PATENT DOCUMENTS

| | | | |
|---|---|---|---|
| 8,728,461 B2 | 5/2014 | Ihara et al. | |
| 2007/0280910 A1 | 12/2007 | Cobb et al. | |
| 2010/0196323 A1 | 8/2010 | Plail et al. | |
| 2011/0104134 A1 | 5/2011 | Ihara | |
| 2011/0189147 A1* | 8/2011 | Garner | ............... A61K 35/74 424/93.45 |

FOREIGN PATENT DOCUMENTS

| | | |
|---|---|---|
| JP | 6-46763 A | 2/1994 |
| JP | 2004-215561 A | 8/2004 |
| JP | 2010-98962 A | 5/2010 |
| KR | 10-2004-0007855 A | 1/2004 |
| KR | 10-2012-0041419 A | 5/2012 |
| WO | 2010/001509 A1 | 1/2010 |

OTHER PUBLICATIONS

Leslie et al, "Trehalose and Sucrose Protect Both Membranes and Proteins in Intact Bacterial during Drying", *Applied and Environmental Microbiology*, 1995, vol. 61, No. 10, pp. 3592-3597.
Weibull, "The Isolation of Protoplast from Bacillus Megaterium by Controlled Treatment with Lysozyme", *J. Bacteriol.* 1953, vol. 66, No. 6, pp. 688-695.
GenBank, Jul. 8, 2000, Accession No. AJ276355, http://www.ncbi.nlm.nih.gov/nuccore/AJ276355.
GenBank, Sep. 18, 2009, Accession No. DQ392987, http://www.ncbi.nlm.nih.gov/nuccore/DQ392987.
Fuller—"Probiotics in man and animals", Journal of Applied Bacteriology 1989, 66, pp. 365-378.
Tanida et al.—"Hypotensive effects of *Lactobacillus johnsonii*LC-1 through autonomic nervous system", *Himan Kenkyu*Journal of the Japan Society for Study of Obesity, vol. 12, No. 3, 2006 (with partial translation).

(Continued)

*Primary Examiner* — Emily A Cordas
(74) *Attorney, Agent, or Firm* — Oblon, McClelland, Maier & Neustadt, L.L.P.

(57) ABSTRACT

This invention provides lactic acid bacteria that have one or more effects selected from among fatigue-ameliorating effect, blood circulation-improving effect, stool odor-reducing effect, and growth-promoting effect and that can be used with high safety. This invention further provides a pharmaceutical preparation comprising, as an active ingredient, lactic acid bacteria that have one or more effects selected from among fatigue-ameliorating effect, blood circulation-improving effect, stool odor-reducing effect, and growth-promoting effect. According to the invention, novel lactic acid bacteria belonging to the *Enterococcus faecium* species having particular mycological properties and exhibiting viability of 40% or higher when freeze-dried in the absence of a dispersion medium and viability of 80% or higher in a probiotic preparation when stored at 40° C. for 4 months, a composition comprising such lactic acid bacteria, an agent for ameliorating fatigue, improving blood circulation, reducing stool odor or promoting growth comprising, as an active ingredient, such composition, and use of such composition for food and other products.

16 Claims, No Drawings

Specification includes a Sequence Listing.

(56) References Cited

OTHER PUBLICATIONS

Hong-Zhou et al.—"*Enterococcus faecium*—Related Outbreak with Molecular Evidence of Transmission from Pigs to Humans", Journal of Clinical Microbiology, Mar. 2002, vol. 40, No. 3, pp. 913-917.

Sundset et al.—"Novel Rumen Bacterial Diversity in Two Geographically Separated Sub-Species of Reindeer", Springer Science, vol. 54, pp. 424-438 (2007).

Extended European Search Report dated Mar. 29, 2016 in Patent Application No. 13825497.4.

"*Enterococcus faecium* 16S rRNA gene, strain DSM20477" Database EMBL, Database Accession No. AJ276355, XP002754381, Jul. 8, 2000, 1 Page.

Albert Manero, et al., "Identification of *Enterococcus spp.* with a Biochemical Key" Applied and Environmental Microbiology, vol. 65, No. 10, XP055250005, Oct. 1999, pp. 4425-4430.

Yan-Bo Wang, et al., "Effect of probiotics, *Enteroccus faecium*, on tilapia (*Oreochromis niloticus*) growth performance and immune response" Aquaculture, vol. 277, No. 3-4, XP022632752, Jun. 3, 2008, pp. 203-207.

Vankerckhoven et al. "Genotypic diversity, antimicrobial resistance, and virulence factors of human isolates and probiotic cultures constituting two intraspecific groups of *Enterococcus faecium* isolates", Applied and Environmental Microbiology 74(14): 4247-4255, 2008.

GeneCore version 6.4.1 sequence search results for SEQ 10 No: 1, database: published applications, Nov. 15, 2015.

\* cited by examiner

LACTIC ACID BACTERIUM

TECHNICAL FIELD

The present invention relates to novel lactic acid bacteria belonging to the *Enterococcus faecium* species, a composition comprising such lactic acid bacteria, an agent comprising such composition as an active ingredient, which is any one of agent selected from among an agent for ameliorating fatigue, an agent for improving blood circulation, an agent for reducing stool odor, and an agent for promoting growth, and use of such composition for food and other products.

BACKGROUND ART

It is said that the enteric environment of people of modern times has deteriorated because of undue stress, unbalanced diet, and irregular living habits, such as lack of sleep. The enteric environment is closely related to the health condition, and common symptoms such as extreme fatigue, and excessive sensitivity to cold, shoulder stiffness, skin problems, and lower back pain caused by blood circulation disorder are considered to result from a deteriorated enteric environment. While such symptoms may be relieved if the enteric environment is brought back to a normal state by modifying irregular living habits, it is not easy for busy people of modern times to modify their living habits. Accordingly, food products, functional food products, and pharmaceutical products that can alleviate such symptoms and are safe, and thus can be routinely and continuously ingested, have been desired.

In the field of animal husbandry, the enteric environment of livestock animals deteriorates due to stresses imposed thereon through group feeding or administration of drugs such as vaccines aimed at an improvement in productivity. This raises problems such as inhibited growth, worsened stool odor, and deteriorated quality of flesh and eggs. While antibiotics or the like have heretofore been used to avoid such problems, antibiotics are administered at low concentrations for a long period of time. Accordingly, the development of antibiotic-resistant strains or the influence of remaining antibiotics on humans has become an issue of concern. Under such circumstances, development of feed or feed additive that has overcome the problems as described above, that is, a feed or feed additive that is highly safe and can be routinely and continuously used, has been awaited in the field of animal husbandry.

In view of enhanced health consciousness of recent years, lactic acid bacteria have drawn attention as components that exert useful biological activity on humans and animals (so-called "functional components"). Up to the present, each of the various types of lactic acid bacteria has been known to exert a particular type of biological activity among a wide variety of biological activity, such as regulation of the functions of the intestines, anti-allergic activity, cholesterol-lowering activity, or antihypertensive activity, upon oral administration to humans or animals (Non-Patent Document 1). In recent years, also, it has been reported that lactic acid bacteria (the *Lactobacillus johnsonii* La1 strain, also referred to as "LC1 lactic acid bacteria") regulate the autonomic nervous system through the central histaminergic system or the hypothalamic suprachiasmatic nucleus in which the circadian clock is present, thereby affecting the blood pressure, body temperature, and other properties (Non-Patent Document 2). Accordingly, research on lactic acid bacterial strains with novel biological activity has been in progress.

While a wide variety of lactic acid bacterial species are known to exert useful biological activity on humans and animals as described above, lactic acid bacteria that would effectively ameliorating fatigue or blood circulation disorder have not yet been discovered. In addition, effects attained by providing livestock animals or the like with lactic acid bacteria that have effects of ameliorating fatigue or blood circulation disorder, in particular, effects of reducing stool odor, or promoting growth have not yet been examined.

PRIOR ART DOCUMENTS

Non-Patent Documents

Non-Patent Document 1: Fuller, R., J. Appl. Bacteriol., 1989; 66: 365
Non-Patent Document 2: Mamoru Tanida et. al., "Hypotensive effects of LC1 lactic acid bacteria mediated by the autonomic nervous system," *Himan Kenkyu* (Journal of the Japan Society for Study of Obesity) Vol. 12, No. 3, 2006

SUMMARY OF THE INVENTION

Problem to be Solved by the Invention

It is an object of the present invention to provide lactic acid bacteria that have one or more effects selected from among fatigue-ameliorating effect, blood circulation-improving effect, stool odor-reducing effect, and growth-promoting effect and that can be used with high safety. It is another object of the present invention to provide a pharmaceutical preparation comprising, as an active ingredient, lactic acid bacteria that have one or more effects selected from among fatigue-ameliorating effect, blood circulation-improving effect, stool odor-reducing effect, and growth-promoting effect.

Means for Solving Problem

The present inventors have conducted concentrated studies in order to attain the above objects. As a result, surprisingly, they discovered that lactic acid bacteria belonging to the *Enterococcus faecium* species having particular mycological properties and exhibiting viability of 40% or higher when freeze-dried in the absence of a dispersion medium and viability of 80% or higher in a probiotic preparation when stored at 40° C. for 4 months would have one or more effects selected from among excellent fatigue-ameliorating effect, blood circulation-improving effect, stool odor-reducing effect, and growth-promoting effect. This has led to the completion of the present invention.

Specifically, the present invention includes the following.
[1] Lactic acid bacteria belonging to the *Enterococcus faecium* species having the mycological properties described below and exhibiting viability of 40% or higher when freeze-dried in the absence of a dispersion medium and viability of 80% or higher in a probiotic preparation when stored at 40° C. for 4 months:
Morphologic Properties
1) gram stain: positive
2) sporulation potential: none
3) motility: none
Physiological Properties
1) catalase: negative
2) sodium pyruvate degradation: positive
3) esculin hydrolysis: positive
4) pyrrolidonyl-2-naphthylamide degradation: positive 5) 2-naphthyl-β-D-galactopyranoside degradation: positive
6) L-leucine-2-naphthyl amide degradation: positive
7) L-alginic acid degradation: positive
8) degradability of various carbohydrates
   D-ribose: +
   D-mannitol: +
   lactose: +
   D-sorbitol: −
   D-trehalose: −
   D-raffinose: −

[2] The lactic acid bacteria belonging to the *Enterococcus faecium* species according to [1] having the chemotaxonomic properties described below:
the lactic acid bacteria have the nucleotide sequence as shown in SEQ ID NO: 1 or a nucleotide sequence showing 90% or higher sequence identity with SEQ ID NO: 1.

[3] The lactic acid bacteria belonging to the *Enterococcus faecium* species according to [1] or [2], which are *Enterococcus faecium* R30 strain (NITS BP-01362), *Enterococcus faecium* R28 strain (MITE BP-01361), or a variant thereof having a DNA mutation.

[4] A composition comprising the lactic acid bacteria according to any of [1] to [3] or a processed product or extraction residue of the lactic acid bacteria.

[5] The composition according to [4], which further comprises a protective agent.

[6] The composition according to [5], wherein the content of the protective agent is 1% by weight or more relative to the dry weight of bacteria.

[7] The composition according to [5], wherein the protective agent is at least one member selected from the group consisting of sucrose, trehalose, sodium glutamate, histidine, and malic acid.

[8] An agent for ameliorating fatigue comprising, as an active ingredient, the composition according to any of [4] to [7].

[9] An agent for improving blood circulation comprising, as an active ingredient, the composition according to any of [4] to [7].

[10] An agent for reducing stool odor comprising, as an active ingredient, the composition according to any of [4] to [7].

[11] An agent for promoting growth comprising, as an active ingredient, the composition according to any of [4] to [7].

[12] A food product comprising the composition according to any of [4] to [7].

[13] A feed or veterinary drug comprising the composition according to any of [4] to [7].

[14] A pharmaceutical product comprising the composition according to any of [4] to [7].

[15] The composition according to any of [4] to [7] used for amelioration or alleviation of at least one condition selected from among fatigue, blood circulation disorder, stool odor, and poor growth.

[16] A method for ameliorating fatigue or blood circulation disorder comprising administering the composition according to any of [4] to [7] to a subject who is in need thereof.

[17] A method for reducing stool odor comprising administering the composition according to any of [4] to [7] to a subject who is in need thereof.

[18] A method for promoting growth comprising administering the composition according to any of [4] to [7] to a subject who is in need thereof.

This patent application claims priority from Japanese Patent Application No. 2012-170136 filed on Jul. 31, 2012, and includes part or all of the contents as disclosed in the description thereof.

Effects of the Invention

The lactic acid bacteria belonging to the *Enterococcus faecium* species having particular mycological properties according to the present invention were found to ameliorate fatigue or blood circulation disorder. Accordingly, a composition comprising the lactic acid bacteria of the present invention or a processed product or extraction residue of such lactic acid bacteria can be used with high safety for a food or pharmaceutical product having effects of ameliorating fatigue or blood circulation disorder. In addition, such lactic acid bacteria were found to have stool odor-reducing effect, and growth-promoting effect. Accordingly, a composition comprising the lactic acid bacteria of the present invention or a processed product or extraction residue of such lactic acid bacteria can be used with high safety as an alternative to an agent such as an antibiotic agent, and such composition can also be used for a feed or feed additive having stool odor-reducing effect, and growth-promoting effect in the field of animal husbandry and other fields.

EMBODIMENTS FOR CARRYING OUT THE INVENTION

Hereafter, the present invention is described in detail.
1. Lactic Acid Bacteria of the Present Invention The lactic acid bacteria of the present invention belong to the *Enterococcus faecium* species exhibiting viability of 40% or higher when freeze-dried in the absence of a dispersion medium and viability of 80% or higher in a probiotic preparation when stored at 40° C. for 4 months, preferably viability of 40% or higher when freeze-dried in the absence of a dispersion medium and viability of 90% or higher in a probiotic preparation when stored at 40° C. for 4 months, and more preferably viability of 40% or higher when freeze-dried in the absence of a dispersion medium and viability of 95% or higher in a probiotic preparation when stored at 40° C. for 4 months.

If bacterial viability is lower than 40% when freeze-dried in the absence of a dispersion medium or it is lower than 80% in a probiotic preparation when stored at 40° C. for 4 months, lactic acid bacteria that have one or more effects selected from among fatigue-ameliorating effect, blood circulation-improving effect, stool odor-reducing effect, and growth-promoting effect cannot be obtained. Thus, such low viability is not preferable.

The term "freeze-dried in the absence of a dispersion medium" in the present invention means that lactic acid bacterial strains in a culture solution obtained by a conventional technique are collected with the use of a centrifuge or the like, the collected strains are dispersed in water without the addition of a dispersion medium, and the resulting dispersion is then freeze-dried. A "dispersion medium" is a substance capable of homogeneously dispersing the collected bacterial strains, and examples thereof include physiological saline, phosphate-buffered saline, and a solution containing a protective agent. The "protective agent" is a substance capable of reducing the damage imposed on a bacterial strain by freezing or dry stress. Examples thereof include trehalose, bovine serum albumin, dried skim milk, sodium glutamate, L-ascorbic acid, histidine, malic acid, whey, glucose, aspartic acid, methionine, starch, dextrin, sucrose, lactose, sodium chloride, and phosphate.

The lactic acid bacteria of the present invention can be obtained by the screening method described below.

(1) Primary Screening (Determination of Bacterial Viability when Freeze-Dried in the Absence of Dispersion Medium)

With the use of a medium in which lactic acid bacteria can grow, strains to be screened are cultured at 37° C. for 24 hours, bacterial strains are separated from the culture solution via centrifugation, the culture solution is removed, and the bacterial strains are then collected. An adequate amount of water is added to the collected bacterial strains without the addition of a dispersion medium, and a concentrate of dispersed bacterial strains is obtained. The total number of viable bacteria in the bacterial concentrate is determined by a conventional technique, such as colony counting. Subsequently, the bacterial concentrate is freeze-dried, and the total number of viable bacteria in the bacterial concentrate is determined by a conventional technique, such as colony counting. Bacterial viability when freeze-dried in the absence of a dispersion medium is then calculated on the basis of the total number of viable bacteria in the bacterial concentrate and the total number of viable bacteria in the concentrate of freeze-dried bacterial strains. Thus, lactic acid bacteria exhibiting viability of 40% or higher are selected.

(2) Secondary Screening (Determination of Bacterial Viability in a Probiotic Preparation when Stored at 40° C. for 4 Months)

The lactic acid bacteria that were found to exhibit viability of 40% or higher when freeze-dried in the absence of a dispersion medium as a result of the primary screening are cultured at 37° C. for 24 hours, bacterial strains are separated from the culture solution via centrifugation, the culture solution is removed, and wet bacterial strains are obtained. After a dispersion medium is added to the wet bacterial strains, the resultant is subjected to freeze-drying, so as to obtain freeze-dried bacterial strains. An excipient is added to the freeze-dried bacterial strains so as to adjust the viable bacterial count to $1.0 \times 10^{10}$ cfu/g. Thus, a probiotic preparation is obtained. The resulting probiotic preparation is stored in an incubator at 40° C. for 4 months, and the viable bacterial count per g of the probiotic preparation is then determined by a conventional technique, such as colony counting. Bacterial viability in a probiotic preparation when stored at 40° C. for 4 months is then determined on the basis of the viable bacterial count in the probiotic preparation before storage ($1.0 \times 10^{10}$ cfu/g) and the viable bacterial count per g of the probiotic preparation. Thus, lactic acid bacteria exhibiting viability of 80% or higher are selected.

Examples of lactic acid bacteria of the present invention obtained by the screening process; i.e., the *Enterococcus faecium* R30 strain (hereafter it is also referred to as the "R30 strain") and the *Enterococcus faecium* R28 strain (hereafter it is also referred to as the "R28 strain"), were deposited on May 16, 2012 at the Patent Microorganisms Depository (NPMD) of the National Institute of Technology and Evaluation (NITE) (2-5-8, Kazusakamatari, Kisarazu-shi, Chiba, 292-0818, Japan) under Accession Numbers NITE P-1362 and NITE P-1361, respectively. These strains were transferred to the international depositary authority under the provisions of the Budapest Treaty on Apr. 24, 2013, under Accession Numbers NITE BP-01362 and NITE BP-01361, respectively.

The *Enterococcus faecium* R30 and R28 strains have the mycological properties described below:
Morphologic Properties
1) gram stain: positive
2) sporulation potential: none
3) motility: none
Physiological Properties
1) catalase: negative
2) sodium pyruvate degradation: positive
3) esculin hydrolysis: positive
4) pyrrolidonyl-2-naphthylamide degradation: positive
5) 2-naphthyl-β-D-galactopyranoside degradation: positive
6) L-leucine-2-naphthyl amide degradation: positive
7) L-alginic acid degradation: positive
8) degradability of various carbohydrates
D-ribose: +
D-mannitol: +
lactose: +
D-sorbitol: –
D-trehalose: –
D-raffinose: –

The mycological properties described above were analyzed using the API® 20 Strep system (manufactured by Sysmex bioMerieux Co., Ltd.). As a result, the strains mentioned above exhibited mycological properties identical to those of *Enterococcus faecium*. Also, as a result of analysis of the entire nucleotide sequence of 16S rDNA, the R30 strain showed 99.8% sequence identity and the R28 strain showed 99.9% sequence identity to the sequence of the *Enterococcus faecium* DSM 20477 strain. However, bacterial viability when freeze-dried in the absence of a dispersion medium and bacterial viability in the probiotic preparation when stored at 40° C. for 4 months are apparently different from those of the DSM20477 strain.

In addition, the lactic acid bacteria of the present invention belonging to the *Enterococcus faecium* species have the chemotaxonomic properties described below:
the lactic acid bacteria have the nucleotide sequence as shown in SEQ ID NO: 1 or a nucleotide sequence showing 90% or higher sequence identity with SEQ ID NO: 1.

It is sufficient for the lactic acid bacteria of the present invention belonging to the *Enterococcus faecium* species to have 90% or higher sequence identity to the nucleotide sequence of 16S rDNA of the DSM20477 strain as shown in SEQ ID NO: 1. Such sequence identity is preferably 95% or higher, more preferably 98% or higher, further preferably 99% or higher, and most preferably 99.5% or 99.8% or higher. Sequence identity of 100% is preferable because lactic acid bacteria that have one or more effects selected from among excellent fatigue-ameliorating effect, blood circulation-improving effect, stool odor-reducing effect, and growth-promoting effect can be obtained. When sequence identity is lower than 90%, lactic acid bacteria that have one or more effects selected from among excellent fatigue-ameliorating effect, blood circulation-improving effect, stool odor-reducing effect, and growth-promoting effect cannot be obtained.

In addition to the R30 strain and the R28 strain described above, variants thereof, and/or descendants thereof, are within the scope of the present invention, provided that such variants and/or descendants have equivalent effects, and such variants and/or descendants can be included in the composition of the present invention instead of the R30 or R28 strain. The term "variant" refers to a lactic acid bacterium having a DNA mutation, and the term "DNA mutation" refers to a treatment that would artificially induce mutagenesis by means of a conventional technique, such as radiation application or the use of a mutagen. A spontaneous DNA mutation is within the scope of the "DNA mutation." The term "descendant" refers to a lactic acid bacterium that inherits its ancestor's genome. In the present invention, the term "descendant" refers to any lactic acid bacterium arising from parent R30 and/or R28 strains and may comprise any natural mutation or DNA recombination due to bacterial cell division or cell proliferation.

The lactic acid bacteria of the present invention can be cultured in any medium as long as such lactic acid bacteria can grow therein. Culture can be carried out in, for example, a test tube, a flask, or a fermenter. For example, an MRS medium that is commonly used for lactic acid bacterial culture may be used, and general lactic acid bacterial culture may be performed under general conditions, although culture conditions are not limited thereto.

2. Composition of the Present Invention and Various Preparations

The composition of the present invention comprises the lactic acid bacteria of the present invention or variants thereof. The lactic acid bacteria or variants thereof contained in the composition of the present invention may be bacterial strains that have not been subjected to any treatment or treated products or extraction residues of the lactic acid bacteria or variants thereof.

Bacterial strains contained in the composition of the present invention may be either viable bacteria or dead bacteria. The term "viable bacteria" used herein refers to lactic acid bacteria remaining alive and the term "dead bacteria" refers to bacterial strains that have been disinfected via heating, pressurization, drug treatment, or another type of treatment.

The term "treated product" used in the present invention refers to a product that has been subjected to at least one treatment selected from among grinding or fragmentation, liquefaction via extraction, concentration, paste preparation, drying (e.g., spray-drying, freeze-drying, vacuum drying, or drum drying), and attenuation of lactic acid bacteria. The term "extraction residue" refers to, for example, a precipitate obtained by treating bacterial strains with boiled water or hot water, obtaining the extract from bacterial strains, and collecting the residue via centrifugation. It should be noted that the "treated product" and the "extraction residue" are not limited thereto.

The composition comprising viable lactic acid bacteria of the present invention can be obtained by, for example, collecting bacterial strains in the culture solution that have been cultured in accordance with a conventional technique, adding a solution of a protective agent to the collected bacterial strains, drying the mixture, and mixing the resultant with an adequate excipient.

Any substance can be used as the protective agent, provided that such substance can reduce damage imposed by freezing or dry stress on bacterial strains. Examples thereof include trehalose, bovine serum albumin, dried skim milk, sodium glutamate, L-ascorbic acid, histidine, malic acid, whey, glucose, aspartic acid, methionine, starch, dextrin, sucrose, lactose, sodium chloride, and phosphate. Such protective agents can be used alone or in combination. For example, bacterial strains in the culture solution that have been cultured in accordance with a conventional technique may be collected via centrifugation, and a solution of a protective agent, such as trehalose, sodium glutamate, histidine, malic acid, or sucrose, may be added to the bacterial strains. The mixing ratio of protective agents is not particularly limited; however, the lower limit for the total amount of the protective agent is 1% by weight or more, preferably 10% by weight or more, and further preferably 100% by weight or more, relative to the dry weight of bacterial strains. If the final concentration of the protective agent is less than 1% by weight relative to the dry weight of bacterial strains, damage imposed by freezing or dry stress on bacterial strains cannot be sufficiently reduced. Accordingly, such low concentration is not preferable.

The composition comprising dead lactic acid bacteria of the present invention can be obtained by, for example, collecting bacterial strains in a culture solution that have been cultured in accordance with a conventional technique, disinfecting the collected bacterial strains, drying the resulting bacterial strains, and mixing the resultant with an adequate excipient.

The term "disinfect" used herein refers to a situation in which bacteria are killed by heating, pressurization, drug treatment, or another type of treatment. Examples thereof include dry-heat disinfection, steam disinfection, high-pressure steam disinfection, chemical disinfection, ultrasonic disinfection, microwave disinfection, and ultraviolet disinfection. The process of "disinfection" may be carried out after drying the collected bacterial strains.

The composition of the present invention has excellent fatigue-ameliorating effect and it can thus be used as an agent for ameliorating fatigue. The agent for ameliorating fatigue of the present invention has effects of preventing or ameliorating a sense of fatigue caused by undue stress, unbalanced diet, or irregular living habits such as lack of sleep, improving motility function, or increasing endurance.

In addition, the composition of the present invention has excellent blood circulation-improving effect, and it can thus be used as an agent for improving blood circulation. The agent for improving blood circulation of the present invention has an action of preventing or ameliorating symptoms such as excessive sensitivity to cold, shoulder stiffness, skin problems, or lower back pain caused by undue stress, unbalanced diet, or irregular living habits such as lack of sleep.

In addition, the composition of the present invention has excellent stool odor-reducing effect, and it can thus be used as an agent for reducing stool odor. The agent for reducing stool odor of the present invention has an action of reducing stool odor of infants who often suffer from enteric imbalance, elderly people, or people who have lost strength. Also, the agent has an action of reducing stool odor of livestock animals that suffer from deteriorated enteric environments because of stress caused by group breeding or drug administration such as vaccination.

Further, the composition of the present invention has excellent growth-promoting effect, and it can thus be used as an agent for promoting growth. The agent for promoting growth of the present invention has an action of promoting growth of infants or suppressing weight loss of elderly people or sick people. Also, the agent has an action of promoting growth of livestock animals that suffer from deteriorated enteric environments because of stress caused by group breeding or drug administration such as vaccination.

In the present invention, fatigue-ameliorating effect can be evaluated by, for example, having a rat to run on a treadmill at 10 m/min, gradually increasing the rate by 5 m/min every 3 minutes, and determining the duration of time until the rat can no longer run (i.e., the maximal running time), as described in the Examples below. If the maximal running time of the rat is prolonged after the test substance has been administered in comparison with the maximal running time of the rat before the test substance has been administered, the test substance is evaluated as having fatigue-ameliorating effect.

In the present invention, blood circulation-improving effect can be evaluated by, for example, having a volunteer to immerse his left hand in cold water at 15° C. for 10 seconds and measuring the skin temperature immediately before the application of cold water stress and 10 minutes after the application of cold water stress with the use of thermography, as described in the Examples below. The skin temperature of the subject measured immediately after the application of cold water stress is compared with that measured 10 minutes after the application of cold water stress. If the difference in the subject's skin temperature therebetween becomes greater as a result of ingestion of the test substance, such test substance is evaluated as having blood circulation-improving effect.

In the present invention, stool odor-reducing effect can be evaluated by, for example, examining the stool odor of a baby chicken, as described in the Examples below. A reduction in stool odor is determined based on the stool odor before administration of the test substance and the stool odor after administration of the test substance, and the test substance is evaluated as having stool odor-reducing effect if the reduction in stool odor is significant. Stool odor may be evaluated by a sensory evaluation, or it may be evaluating by measuring, for example, the concentration of acetic acid gas in a stool sample.

In the present invention, growth-promoting effect can be evaluated by, for example, measuring body weights of mice, as described in the Examples below. If the body weight of a mouse to which the test substance has been administered is greater than that of a mouse to which the test substance has not been administered, the test substance is evaluated as having growth-promoting effect.

3. Use of the Composition of the Present Invention

The composition of the present invention can be used for a food product, functional food product or supplement, feed (including pet food), veterinary drug, or pharmaceutical product.

When the composition of the present invention is ingested on a routine basis in the form of a food product, the form of the food product containing the composition of the present invention is not particularly limited. Examples thereof include common forms of food products, such as an edible oil composition, cooking oil, spray oil, butter, margarine, shortening, whip cream, concentrated milk, whitener, dressing, pickling liquid, bread, cake, pie, cookie, Japanese-style confectionary, snack, fried confectionary, chocolate, chocolate confectionary, rice confectionary, roux, sauce, baste, topping, ice confectionary, noodles, bakery mix, fried food product, processed meat product, other processed product such as soybean curd or konjac, fishery paste product, frozen food product, such as frozen entrée, frozen livestock food product, or frozen agricultural food product, cooked rice, jam, cheese, cheese-based food, cheese-like food product, gum, candy, fermented milk, canned food, and beverage. Alternatively, it may be in the form of a fermented food product prepared by fermenting a common form of a food product with the use of the lactic acid bacteria of the present invention or variants thereof having a DNA mutation.

When the composition of the present invention is prepared in the form of a food product, the content of lactic acid bacteria or a treated product or extraction residue thereof is not particularly limited. For example, the lower limit of such content is 0.00001% by weight, preferably 0.001% by weight, and further preferably 0.1% by weight in a food product, and the upper limit thereof is 100% by weight, preferably 50% by weight, and further preferably 30% by weight in a food product.

The composition of the present invention can also be prepared in the form of a supplement, such as a capsule or tablet, and it can be used for Food With Health Claims, such as Food for Specified Health Uses or Food with Nutrient Function Claims, or functional food products, such as health food products or nutritional supplements. The use thereof can be indicated as use for prevention or amelioration of fatigue, improvement of motility function, improvement of endurance, and/or prevention or amelioration of excessive sensitivity to cold, shoulder stiffness, skin problems, or lower back pain, and/or reduction or moderation of stool odor, and/or promotion of growth. To this end, the composition of the present invention is administered to a subject once or in several separate instances per day, so that an adult subject can ingest at least 0.01 mg and preferably at least 1 mg of lactic acid bacteria or a treated product or extraction residue thereof per kg of the body weight of the subject per day. The maximal amount thereof that can be administered is 1,000 mg and preferably 300 mg thereof per kg of the body weight of an adult per day.

When the composition of the present invention is used in the form of a functional food product or supplement, the dosage form thereof is not particularly limited. Examples thereof include capsules, syrups, tablets, pills, powders, granules, beverages, injection preparations, infusion solutions, nasal drops, eye drops, suppositories, adhesive skin patches, and sprays, although the dosage form is not limited thereto. When preparing a pharmaceutical preparation, another pharmaceutically acceptable agent, such as an excipient, disintegrator, lubricant, antioxidant, coloring agent, anti-coagulant, absorption accelerator, solubilizer, or stabilizer, can be adequately added.

When the composition of the present invention is used for a feed (including pet food) or a veterinary drug, the lactic acid bacteria or a treated product or extraction residue thereof are used as main raw materials. Raw materials used for a common feed mixture may be adequately added in accordance with animal species, growth stage, or breeding environment, such as the area of breeding. Examples of such raw materials include cereals and processed cereals (e.g., maize, milo, barley, wheat, rye, oat, millet, flour, and wheat germ powder), cereal grain by-products (e.g., bran, rice bran, and corn gluten feed), vegetable oil meals (e.g., soybean oil meal, sesame oil meal, cottonseed oil meal, peanut meal, sunflower seed oil, and safflower oil meal), animal-derived raw materials (e.g., dried skim milk, fish meal, and bone-meal feed), minerals (e.g., calcium carbonate, calcium phosphate, salt, and anhydrous silicic acid), vitamins (e.g., vitamin A, vitamin D, vitamin E, vitamin K, vitamin B1, vitamin B2, vitamin B6, vitamin B12, calcium pantothenate, nicotinic-acid amide, and folic acid), amino acids (e.g., glycine and methionine), yeast such as brewer's yeast, and fine powders of inorganic substances (e.g., crystalline cellulose, talc, silica, white mica, and zeolite).

The feed of the present invention may comprise, in addition to the raw materials of feed described above, a feed additive that is commonly used for a feed mixture, such as an excipient, filler, binder, thickener, emulsifier, coloring agent, aroma chemical, food additive, or seasoning agent, and other components, such as an antibiotic, disinfectant, anthelmintic, or antiseptic agent, according to need.

The forms of the feed of the present invention are not particularly limited, and examples thereof include powders, granules, pastes, pellets, capsules (hard or soft capsules), and tablets. Animals to which the feed of the present invention is to be given are not particularly limited, and examples thereof include livestock animals, such as cows, horses, pigs, and sheep, poultry, such as chickens including broilers and layer chickens, turkeys, and hybrids between Mallards and domestic ducks, experimental animals, such as mice, rats, and guinea pigs, and pet animals, such as dogs and cats.

In such case, the composition of the present invention is administered in a single instance or several separate instances per day, so that at least 0.001 mg, preferably 0.01 mg, and further preferably 0.1 mg of lactic acid bacteria or a treated product or extraction residue thereof can be administered to a target animal per kg of the body weight thereof, regardless of the animal species. The maximal amount thereof that can be administered is 1,000 mg and preferably 500 mg per kg of the body weight of an animal per day.

When the composition of the present invention is used for a pharmaceutical product, the dosage form thereof is not particularly limited. Examples thereof include capsules, syrups, tablets, pills, powders, granules, drinkable preparations, injection preparations, infusion solutions, nasal drops, eye drops, suppositories, adhesive skin patches, and sprays. When preparing a pharmaceutical preparation, another pharmaceutically acceptable agent, such as an excipient, disintegrator, lubricant, binder, antioxidant, coloring agent, anticoagulant, absorption accelerator, solubilizer, or stabilizer, can be adequately added.

The amount of the composition of the present invention administered in the form of a pharmaceutical product may be determined in accordance with the amount of the functional food product or supplement to be administered.

EXAMPLES

Hereafter, the present invention is described in greater detail with reference to the examples, although the present invention is not limited to these examples. In the examples, lactic acid bacteria was selected through the methods of primary screening and secondary screening described below, and biological activity was evaluated by evaluating fatigue-ameliorating effect, blood circulation-improving effect, stool odor-reducing effect, and growth-promoting effect.

<Primary screening method>

Lactic acid bacteria were cultured in 10 ml of MRS liquid medium (a solution of 0.52 g of MRS broth (manufactured by Kanto Chemical Co., Inc.) dissolved in 10 ml of water, sterilized in an autoclave at 121° C. for 15 minutes) at 37° C. for 24 hours to obtain a preculture solution. The preculture solution (1 ml) was added to 100 ml of MRS liquid medium, and culture was conducted at 37° C. for 24 hours. After the completion of culture, the culture product was centrifuged at 8,000 rpm for 10 minutes to separate bacterial strains from the culture solution. The bacterial strains were washed with 100 ml of sterile water and centrifuged again to separate the bacterial strains from the sterile water. Fresh sterile water (2 ml) was added to the bacterial strains to obtain a bacterial concentrate. The bacterial concentrate (0.1 ml) was suspended in 0.9 ml of physiological saline, an MRS agar medium (this MRS agar medium was prepared by dissolving 1.24 g of an MRS agar medium (manufactured by Kanto Chemical Co., Inc.) in 20 ml of water, sterilizing the resultant in an autoclave at 121° C. for 15 minutes, and introducing the resultant into a sterile petri dish (90 φ×20), followed by solidification) was coated with 0.1 ml of a bacterial solution diluted $10^6$-fold with physiological saline, and culture was conducted at 37° C. for 2 days. The developed colonies were counted to determine the total viable bacterial count in the bacterial concentrate. The bacterial concentrate was freeze-dried in a freeze-dryer, the VIRTIS® ADVANTAGE PLUS® (freezing conditions: −30° C. for 12 hours; drying conditions: 10 x $10^{-1}$ torr at a shelf temperature of 20° C. for 48 hours) to obtain freeze-dried bacterial strains. The freeze-dried bacterial strains (20 mg) were dispersed in 1 ml of physiological saline to obtain a bacterial suspension, and the resulting bacterial suspension was diluted $10^6$-fold with physiological saline. An MRS agar medium was coated with 0.1 ml of the resulting diluent, culture was conducted at 37° C. for 2 days, and the developed colonies were counted to determine the total viable bacterial count in the freeze-dried bacterial strains. Bacterial viability when freeze-dried in the absence of a dispersion medium was calculated using the equation shown below, and lactic acid bacteria exhibiting viability of 40% or higher were selected.

Bacterial viability when freeze-dried in the absence of dispersion medium (%)=(total number of viable bacteria among dry bacteria/total number of viable bacteria in bacterial concentrate)×100

<Secondary Screening Method>

The lactic acid bacteria selected via primary screening method were cultured in 10 ml of MRS liquid medium at 37° C. for 24 hours to obtain a preculture solution. The preculture solution (10 ml) was added to 1 liter of MRS liquid medium and culture was conducted at 37° C. for 24 hours. After the completion of culture, the culture product was centrifuged at 8,000 rpm for 10 minutes to separate bacterial strains from the culture solution. The bacterial strains were washed with 1 liter of sterile water and centrifuged again to separate the bacterial strains from sterile water. Sterile water was added to the bacterial strains so as to adjust the volume of the bacterial solution to 20 ml. Thus, a bacterial concentrate was obtained. A solution (2 ml) of a protective agent comprising 0.4% by weight of sucrose, 0.2% by weight of trehalose, 0.2% by weight of sodium glutamate, 0.2% by weight of histidine, and 0.2% by weight of malic acid was added to the bacterial concentrate, and the resultant was freeze-dried under the same conditions as described above to obtain freeze-dried bacterial strains. The freeze-dried bacterial strains were mixed with dextrin to adjust the viable bacterial count to $1.0 \times 10^{10}$ cfu/g, and a probiotic preparation was thus obtained. The probiotic preparation was introduced into separate polyethylene bags with zippers (Unipac B-8, manufactured by Seisannipponsha Ltd.) in amounts of 10 g each, packed into aluminum pouches (Lamizip, manufactured by Seisannipponsha Ltd.) each containing 1 g of silica gel (manufactured by Fuji Silysia Chemical Ltd.), and heat-sealed. The resultant was designated as a storage sample. The storage sample was stored in an incubator at 40° C. for 4 months, 100 mg of a probiotic preparation was dispersed in 1 ml of physiological saline to prepare a bacterial suspension, the suspension was diluted $10^7$-fold with physiological saline, and an MRS agar medium was coated with 0.1 ml of the resulting diluent. Culture was conducted at 37° C. for 2 days, the developed colonies were counted, and bacterial viability in the probiotic preparation when stored at 40° C. for 4 months was calculated using the equation below. Thus, lactic acid bacteria exhibiting viability of 80% or higher were selected.

Bacterial viability in probiotic preparation when stored at 40° C. for 4 months (%)=(viable bacterial count per g of probiotic preparation after storage at 40° C. for 4 months/$1.0 \times 10^{10}$)×100

<Evaluation of Fatigue-ameliorating Effect>

Fatigue-ameliorating effect was evaluated by having rats (7- to 10-week-old SD male rats (a group: n=10)) to run on a treadmill (5 lanes, MK-680S-02A, Muromachi Kikai Co., Ltd.) at 10 m/min, gradually increasing the rate by 5 m/min every 3 minutes, and determining the duration of time until the rats could no longer run (i.e., the maximal running time). The maximal running time was measured before administration of the test substance and 2 hours after administration of the test substance, and the maximal running time measured before administration of the test substance was subtracted from the maximal running time measured 2 hours after administration of the test substance to determine the difference in the maximal running time before and after the administration of the test substance. Fatigue-ameliorating effect was evaluated on the basis of whether or not the difference between the maximal running time measured before administration of the test substance and that measured after administration of the test substance had increased as a result of the administration of the test substance.

<Evaluation of Blood Circulation-improving Effect>

Blood circulation-improving effect was evaluated by having 20- to 50-year-old healthy males (a group: n=5) to ingest the test substance for 1 week and subjecting them to the cold water stress test. The cold water stress test was performed by having subjects to immerse their left hands in cold water at 15° C. for 10 seconds and measuring the skin temperature immediately thereafter and 10 minutes thereafter with the use of thermography (TVS 600, manufactured by Nippon Avionics Co., Ltd.). The average skin temperature measured immediately after cold water stress application was subtracted from the average skin temperature measured 10 minutes after cold water stress application (i.e., the difference in average skin temperature), and blood circulation-improving effect was evaluated on the basis of whether or not the difference in average skin temperature had significantly increased as a result of ingestion of the test substance. The average skin temperature was determined by measuring the skin temperature at 3 sites; i.e., the tip of the middle finger on the opisthenar side, the midpoint of the proximal phalanx of the middle finger, and the midpoint of the third metacarpal bone.

<Evaluation of Stool Odor-reducing Effect>

Stool odor-reducing effect was evaluated by administering the test feed to 8-day-old male baby chickens (a group: n=10) for 6 days, examining stool odors of samples before the initiation of the test and after the completion of the test, and determining the reduction in stool odor after the completion of the test. Stool odor-reducing effects was evaluated on the basis of whether or not the reduction in stool odor of the group to which the test feed containing the test substance (i.e., a feed mixture containing the test substance) had been administered was greater than that of the group to which the test feed without the test substance (i.e., the reference feed) had been administered. Stool odor was evaluated in terms of an odor index, hydrogen sulfide gas concentration, and acetic acid gas concentration of stool samples. Reductions in the odor index, hydrogen sulfide gas concentration, and acetic acid gas concentration of stool samples after the test were determined. The odor index values were determined by suspending 1 g of a stool sample in 100 ml of odorless distilled water, allowing the sample to stand at 25° C. for 30 minutes, diluting the sample to 1/10th initial concentration, and analyzing the resulting test solution using a three-point comparison-type flask method. Hydrogen sulfide gas concentration and acetic acid gas concentration were determined by mounting 100 g of stool sample on a glass petri dish, introducing the petri dish into a 10-liter polystyrene bag, creating a vacuum in the bag, filling the bag with odorless air purified with the aid of active carbon to hermetically seal the bag, allowing the resultant to stand at room temperature (about 22° C.) for 1 hour, and determining hydrogen sulfide gas concentration and acetic acid gas concentration in the bag with the use of a gas-detecting tube. The collected stool samples were hermetically sealed and stored at −80° C. before the test.

<Evaluation of Growth-promoting Effect>

Growth-promoting effect was evaluated by administering the test feed to 5-week-old ICR male mice (a group: n=10) for 1 month and measuring their body weighs upon completion of the test. Growth-promoting effect was evaluated on the basis of whether or not body weights of the group of mice to which the test feed containing the test substance (i.e., a feed mixture containing the test substance) had been administered were greater than those of the group of mice to which the test feed without the test substance (i.e., the reference feed) had been administered. In order to measure the amount of feed that each mouse had ingested during the test, mice were individually bred and allowed to freely ingest the test feed with the use of a powder feeder equipped with Roden CAFE (Oriental Yeast Co., Ltd.).

In the following examples, the *Enterococcus faecium* DSM20477 strain, which is a reference strain of *Enterococcus faecium*, is referred to as the "reference strain." When the reference strain is freeze-dried in the absence of a dispersion medium, the bacterial viability is 25%. The bacterial viability in a probiotic preparation is 40% when stored at 40° C. for 4 months.

Example 1 Screening of R30 Strain

Lactic acid bacterial strains (125 strains: Isolate 1 to Isolate 125) separated from food materials and the like were subjected to the process of primary screening described above, and the viability of each isolate when freeze-dried in the absence of a dispersion medium was determined.

Among 125 strains, Isolate 17 and Isolate 82 exhibited viability of 40% or higher when freeze-dried in the absence of a dispersion medium.

Subsequently, Isolate 17 and Isolate 82 were subjected to the process of secondary screening described above, and the viability of each thereof in a probiotic preparation when stored at 40° C. for 4 months was determined. The results are shown in Table 1.

TABLE 1

| Strain | Viability (%) |
|---|---|
| Isolate 17 | 60 |
| Isolate 82 | 100 |

Isolate 82 was found to exhibit viability of 80% or higher in a probiotic preparation when stored at 40° C. for 4 months.

Mycological properties of Isolate 82 were examined using the API® 20 Strep system (manufactured by Sysmex bioMerieux Co., Ltd.), and Isolate 82 was found to exhibit mycological properties identical to those of *Enterococcus faecium*. Further, the nucleotide sequence of 16S rDNA of Isolate 82 was found to exhibit sequence identity of 99.8% to the sequence as shown in SEQ ID NO: 1. Thus, Isolate 82 was found to belong to the *Enterococcus faecium* species. In the following examples, Isolate 82 is referred to as the R30 strain.

Example 2 Measurement of Fatigue-ameliorating Effect of R30 Strain

In accordance with the method described with reference to the process of secondary screening described above, freeze-dried bacterial strains of the R30 strain and the reference strain were prepared, and the freeze-dried bacterial strains were mixed with dextrin to adjust the viable bacterial count to $5.0 \times 10^{10}$ cfu/g. The R30 strain administration group to which a probiotic preparation of the R30 strain was administered in an amount of 1 g/kg, the reference strain administration group to which a probiotic preparation of the reference strain was administered in an amount of 1 g/kg, and the dextrin administration group to which dextrin was administered in an amount of 1 g/kg were subjected to evaluation regarding fatigue-ameliorating effect as described above. The results thereof are shown in Table 2.

TABLE 2

|  | Difference in maximal running time (sec) |
| --- | --- |
| Dextrin administration group | −15 |
| Reference strain administration group | −10 |
| R30 strain administration group | 35 |

As is apparent from Table 2, the R30 strain administration group exhibited a difference in the maximal running time before and after the administration of the test substance significantly greater than that of the dextrin administration group and the reference strain administration group. Thus, the R30 strain was found to have fatigue-ameliorating effect.

Example 3 Measurement of Blood Circulation-improving Effect of R30 Strain

The R30 strain ingestion group that was to ingest 1 g of a probiotic preparation of the R30 strain prepared in Example 2 every day, the reference strain ingestion group that was to ingest 1 g of a probiotic preparation of the reference strain prepared in Example 2 every day, and the dextrin ingestion group that was to ingest 1 g of dextrin every day were subjected to evaluation of blood circulation-improving effect as described above. The results thereof are shown in Table 3.

TABLE 3

|  | Difference in average skin temperature after administration of test substance (° C.) |
| --- | --- |
| Dextrin ingestion group | 3 |
| Reference strain ingestion group | 3 |
| R30 strain ingestion group | 7 |

As is apparent from Table 3, the R30 strain ingestion group exhibited significantly higher average skin temperature after the ingestion of the test substance for a week than the dextrin ingestion group and the reference strain ingestion group. Thus, the R30 strain was found to have blood circulation-improving effect.

Example 4 Measurement of Stool Odor-reducing Effect of R30 Strain

In accordance with the method described with reference to the process of secondary screening described above, freeze-dried strains of R30 strain were prepared and a probiotic preparation thereof was prepared by mixing the freeze-dried bacterial strains with dextrin to adjust the viable bacterial count to $1.0 \times 10^{10}$ cfu/g. The probiotic preparation of the R30 strain was mixed with the reference feed (i.e., the reference feed for early-stage broiler fattening, manufactured by Nippon Formula Feed Manufacturing Company Limited) in an amount of 0.3% by weight thereof, and the resulting test feed (i.e., a feed mixture containing R30 strain) was evaluated in terms of stool odor-reducing effect as described above. The results thereof are shown in Table 4.

TABLE 4

|  | Reduction in odor index (%) | Reduction in hydrogen sulfide gas concentration (%) | Reduction in acetic acid gas concentration (%) |
| --- | --- | --- | --- |
| Reference feed | 0 | 25 | 13 |
| Feed mixture containing R30 strain | 26 | 50 | 43 |

As is apparent from Table 4, the group to which a feed mixture containing R30 strain had been administered exhibited greater reductions in the odor index, hydrogen sulfide gas concentration, and acetic acid gas concentration, compared with the reference feed group. Thus, the R30 strain was found to have stool odor-reducing effect.

Example 5 Measurement of Growth-promoting Effect of R30

The probiotic preparation of the R30 strain prepared in Example 4 was mixed with the reference feed (powder feed CE-2, manufactured by CLEA Japan, Inc.) in an amount of 0.1% by weight thereof to prepare a test feed (i.e., a feed mixture containing R30 strain), and the resulting test feed was evaluated in terms of growth-promoting effect as described above. After the completion of the test, body weights of the group of mice to which the reference feed had been administered were measured and designated as 100%, and the proportion of the body weight of the group to which the feed mixture containing R30 strain had been administered to that of the group to which the reference feed had been administered was determined. The results thereof are shown in Table 5.

TABLE 5

|  | Proportion to body weight (%) |
| --- | --- |
| Reference feed | 100 |
| Feed mixture containing R30 strain | 107 |

As is apparent from Table 5, the body weight of the group to which the feed mixture containing R30 strain had been administered was 107% relative to the body weight of the group to which the reference feed had been administered. That is, the R30 strain was found to have growth-promoting effect. The average amounts of feed ingested by the reference feed group and the group to which a feed mixture containing R30 strain had been administered during the test were 200 g and 199 g, respectively. That is, there were no significant differences. Thus, the R30 strain was found to have effects of improving feed efficiency.

As is apparent from the results shown in Table 2 to Table 5, the R30 strain has fatigue-ameliorating effect, blood circulation-improving effect, stool odor-reducing effect, and growth-promoting effect. Thus, the present inventors decided to further screen for lactic acid bacteria of the *Enterococcus faecium* species having mycological properties identical to those of the R30 strain, exhibiting viability of 40% or higher when freeze-dried in the absence of a dispersion medium, and exhibiting 80% or higher bacterial viability in a probiotic preparation when stored at 40° C. for 4 months.

Example 6 Screening of R28 strain

Lactic acid bacterial strains separated from food materials and the like were examined with the use of the API® 20 Strep system (manufactured by Sysmex bioMerieux Co., Ltd.) to select 10 strains exhibiting mycological properties identical to those of the *Enterococcus faecium* species (the *Enterococcus faecium* strains 1 to 10). The selected strains were subjected to the process of primary screening described above, three strains exhibiting 40% or higher viability when freeze-dried in the absence of a dispersion medium (i.e., *Enterococcus faecium* 1, *Enterococcus faecium* 2, and *Enterococcus faecium* 3) were subjected to secondary screening, and bacterial viability in a probiotic preparation when stored at 40° C. for 4 months was determined. The results thereof are shown in Table 6.

TABLE 6

| Strain | Bacterial viability in the absence of dispersion medium (%) | Bacterial viability after storage at 40° C. for 4 months (%) |
| --- | --- | --- |
| *Enterococcus faecium* 1 | 45 | 80 |
| *Enterococcus faecium* 2 | 50 | 60 |
| *Enterococcus faecium* 3 | 40 | 45 |
| *Enterococcus faecium* 4 | 34 | — |
| *Enterococcus faecium* 5 | 30 | — |
| *Enterococcus faecium* 6 | 28 | — |
| *Enterococcus faecium* 7 | 28 | — |
| *Enterococcus faecium* 8 | 25 | — |
| *Enterococcus faecium* 9 | 25 | — |
| *Enterococcus faecium* 10 | 23 | — |

As is apparent from the results shown in Table 6, *Enterococcus faecium* 1 exhibits viability of 40% or higher when freeze-dried in the absence of a dispersion medium and viability of 80% or higher in a probiotic preparation when stored at 40° C. for 4 months. The entire nucleotide sequence of 16S rDNA of *Enterococcus faecium* 1 was analyzed and, as a result, it was found to exhibit 99.9% sequence identity to the sequence as shown in SEQ ID NO: 1. In the following examples, *Enterococcus faecium* 1 is referred to as the R28 strain.

Example 7 Measurement of Fatigue-ameliorating Effect and Blood Circulation-improving Effect of R28 Strain Fatigue-ameliorating effect and blood circulation-improving effect of the R28 strain obtained in Example 6 were examined in the same manner as in Example 2 and Example 3. The *Enterococcus faecium* 2 and *Enterococcus faecium* 4 strains were designated as control samples for the R28 strain. The results thereof are shown in Table 7.

TABLE 7

| Strain | Fatigue-ameliorating effect Difference in maximal running time (sec) | Blood circulation-improving effect | |
| --- | --- | --- | --- |
| | | Difference in average skin temperature before administration (° C.) | Difference in average skin temperature after administration (° C.) |
| R28 strain | 20 | 3 | 6 |
| *Enterococcus faecium* 2 | −10 | 3 | 4 |
| *Enterococcus faecium* 4 | −10 | 3 | 4 |

As is apparent from Table 7, the R28 strain has significant fatigue-ameliorating effect and blood circulation improvement, compared with *Enterococcus faecium* 2 and *Enterococcus faecium* 4. As a result, lactic acid bacteria belonging to the *Enterococcus faecium* species were found to have particular mycological properties and excellent effects; that is, such lactic acid bacteria would exhibit viability of 40% or higher when freeze-dried in the absence of a dispersion medium and viability of 80% or higher in a probiotic preparation when stored at 40° C. for 4 months.

Example 8 Measurement of Stool Odor-reducing Effect and Growth-promoting Effect of R28 Strain Stool odor-reducing effect and growth-promoting effect of the R28 strain were examined in the same manner as in Example 4 and Example 5. The results thereof are shown in Table 8.

TABLE 8

| | Stool odor-reducing effect | | | Growth-promoting effect. |
| --- | --- | --- | --- | --- |
| | Reduction in odor index (%) | Reduction in hydrogen sulfide gas concentration (%) | Reduction in acetic acid gas concentration (%) | Proportion to body weight (%) |
| Reference feed | 0 | 25 | 13 | 100 |
| Feed mixture containing R28 strain | 20 | 45 | 50 | 106 |

As is apparent from Table 8, in comparison with the group to which only the reference feed had been administered, the group to which a feed mixture containing R28 strain exhibits remarkable stool odor-reducing effect and significant growth-promoting effect. As a result of measurement of effects of the R28 strain for growth promotion, also, the average total amount of feed ingested during the test period was 200 g in both the group to which the reference feed had been administered and the group to which the feed mixture containing the R28 strain had been administered. Thus, the R28 strain was found to have effects of improving feed efficiency.

Example 9 Production of Probiotic Preparation Using R30 Strain and R28 Strain

The R30 strain was cultured in 1 liter of MRS liquid medium at 37° C. for 24 hours. After the completion of culture, the bacterial strains were centrifuged, washed with 1 liter of sterile water, and then centrifuged again to separate the bacterial strains from sterile water. A solution of a protective agent comprising sucrose, trehalose, sodium glutamate, histidine, and malic acid dissolved in amounts of 0, 1, 3, 10, 100, 1,000, and 10,000% by weight, respectively, relative to the dry weight of bacteria in the bacterial concentrate was added to the bacterial concentrate, the volume of which had been adjusted to 20 ml with sterile water, and the resultant was then freeze-dried. The freeze-dried bacterial strains were mixed with dextrin to adjust the viable bacterial count to $1.0 \times 10^{10}$ cfu/g, a probiotic preparation was prepared, and bacterial viability in a probiotic preparation when stored at 40° C. for 4 months was determined. The R28 strain was subjected to a similar experiment. The results thereof are shown in Table 9.

TABLE 9

| Amount of protective agent added (wt %) | Viability after storage at 40° C. for 4 months (%) | |
|---|---|---|
| | R30 strain | R28 strain |
| 10000 | 100 | 100 |
| 1000 | 100 | 100 |
| 100 | 100 | 100 |
| 10 | 100 | 95 |
| 3 | 100 | 80 |
| 1 | 85 | 80 |
| 0 | 45 | 36 |

As is apparent from the results shown in Table 9, bacterial viability in a probiotic preparation when stored at 40° C. for 4 months was improved with the addition of 1% by weight or more protective agent relative to the dry weight of bacteria. Also, by increasing the amount of the protective agent, from 3% by weight to 10% by weight and then to 100% by weight, relative to the dry weight of bacteria, bacterial viability in a probiotic preparation when stored at 40° C. for 4 months was improved.

INDUSTRIAL APPLICABILITY

The present invention is applicable in the field of manufacture of food products such as functional food products and supplements, feeds, and pharmaceutical products utilizing lactic acid bacteria.

All publications, patents, and patent applications cited herein are incorporated herein by reference in their entirety.

The invention claimed is:

1. A composition, comprising:
spray-dried, freeze-dried, vacuum dried, and/or drum dried lactic acid bacterial cells belonging to the *Enterococcus faecium* species; and
a protective agent,
wherein the lactic acid bacterial cells exhibit viability of 40% or higher after being freeze-dried, spray-dried, vacuum dried, and/or drum dried in the absence of the protective agent and viability of 80% or higher after being freeze-dried, spray-dried, vacuum dried, and/or drum dried in the presence of the protective agent after being stored at 40° C. for 4 months, wherein the addition of an effective amount of protective agent increases viability of the lactic acid bacterial cells when freeze-dried, spray-dried, vacuum dried and/or drum dried and stored at 40° C. for 4 months,
wherein the lactic acid bacterium is gram positive, has no sporulation potential, has no motility, does not have catalase, is capable of degrading sodium pyruvate, pyrrolidonyl-2-naphthylamide, 2-naphthyl-β-D-galactopyranoside, L-leucine-2-naphthylamide, L-alginic acid, D-ribose, D-mannitol, and lactose, is capable of hydrolyze esculin, and is incapable of degrading D-sorbitol, D-trehalose, and D-raffinose,
wherein the lactic acid bacterium has a 16S ribosomal DNA having the nucleotide sequence of SEQ ID NO: 1 or a nucleotide sequence having 99% or higher sequence identity with the nucleotide sequence of SEQ ID NO: 1, and wherein the lactic acid bacterium is at least one selected from the group consisting of *Enterococcus faecium* R30 having the accession number NITE BP-01362, *Enterococcus faecium* R28 having the accession number NITE BP-01361 and a variant thereof.

2. The composition of claim 1, wherein an amount of the protective agent in the composition is 1% by weight or more relative to a dry weight of the lactic acid bacterial cells.

3. The composition of claim 1, wherein the protective agent is at least one selected from the group consisting of sucrose, trehalose, sodium glutamate, histidine, and malic acid.

4. The composition of claim 1, wherein lactic acid bacterial cells in the composition are freeze dried.

5. The composition of claim 3, wherein an amount of the protective agent in the composition is 1% by weight or more relative to a dry weight of the lactic acid bacterial cells.

6. The composition of claim 1, wherein the lactic acid bacterium comprises a dead bacterium.

7. The composition of claim 3, wherein an amount of the protective agent in the composition is 10% by weight or more relative to a dry weight of the lactic acid bacterial cells.

8. A composition, comprising:
spray-dried, freeze-dried, vacuum dried, and/or drum dried lactic acid bacterial cells belonging to the *Enterococcus faecium* species; and
a protective agent,
wherein the composition is obtained by a process comprising culturing the lactic acid bacterial cells, adding the protective agent, thereby obtaining a mixture, and spray-drying, freeze-drying, vacuum drying, and/or drum drying the mixture,
wherein the lactic acid bacterial cells exhibit viability of 40% or higher after being freeze-dried, spray-dried, vacuum dried, and/or drum dried in the absence of the protective agent and viability of 80% or higher after being freeze-dried, spray-dried, vacuum dried, and/or drum dried in the presence of the protective agent after being stored at 40° C. for 4 months, wherein the addition of an effective amount of the protective agent increases viability of the lactic acid bacterial cells when freeze-dried, spray-dried, vacuum dried and/or drum dried and stored at 40° C. for 4 months,
wherein the lactic acid bacterium is gram positive, has no sporulation potential, has no motility, does not have catalase, is capable of degrading sodium pyruvate, pyrrolidonyl-2-naphthylamide, 2-naphthyl-β-D-galactopyranoside, L-leucine-2-naphthylamide, L-alginic acid, D-ribose, D-mannitol, and lactose, is capable of hydrolyze esculin, and is incapable of degrading D-sorbitol, D-trehalose, and D-raffinose,
wherein the protective agent is at least one selected from the group consisting of sucrose, trehalose, sodium glutamate, histidine, and malic acid,
wherein an amount of the protective agent in the composition is 1% by weight or more relative to a dry weight of the lactic acid bacterium,
wherein the lactic acid bacterium has a 16S ribosomal DNA having the nucleotide sequence of SEQ ID NO:

1 or a nucleotide sequence having 99% or higher sequence identity with the nucleotide sequence of SEQ ID NO: 1, and wherein the lactic acid bacterium is at least one selected from the group consisting of *Enterococcus faecium* R30 having the accession number NITE BP-01362, *Enterococcus faecium* R28 having the accession number NITE BP-01361 and a variant thereof.

9. The composition of claim 8, wherein the amount of the protective agent in the composition is 10% by weight or more relative to a dry weight of the lactic acid bacterial cells.

10. A method for ameliorating fatigue, comprising:
    administering the composition of claim 1 to a subject in need thereof.

11. A method for improving blood circulation, comprising:
    administering the composition of claim 1 to a subject in need thereof.

12. A method for reducing stool odor, comprising:
    administering the composition of claim 1 to a subject in need thereof.

13. A method for promoting growth, comprising:
    administering the composition of claim 1 to a subject in need thereof.

14. A food product, comprising:
    the composition of claim 1.

15. A feed or a veterinary drug, comprising:
    the composition according to claim 1.

16. A pharmaceutical product, comprising:
    the composition according to claim 1.

* * * * *

SEQUENCE LISTING

<160> NUMBER OF SEQ ID NOS: 1

<210> SEQ ID NO 1
<211> LENGTH: 1515
<212> TYPE: DNA
<213> ORGANISM: Enterococcus faecium

<400> SEQUENCE: 1

```
gacgaacgct ggcggcgtgc ctaatacatg caagtcgaac gcttcttttt ccaccggagc      60
ttgctccacc ggaaaaagag gagtggcgaa cgggtgagta cacgtgggt aacctgccca      120 tcagaagggg ataacacttg gaaacaggtg ctaataccgt ataacaatcg aaaccgcatg      180
gttttgattt gaaaggcgct ttcgggtgtc gctgatggat ggacccgcgg tgcattagct      240
agttggtgag gtaacggctc accaaggcca cgatgcatag ccgacctgag agggtgatcg      300
gccacattgg gactgagaca cggcccaaac tcctacggga ggcagcagta gggaatcttc      360
ggcaatggac gaaagtctga ccgagcaacg ccgcgtgagt gaagaaggtt ttcggatcgt      420
aaaactctgt tgttagagaa gaacaaggat gagagtaact gttcatccct tgacggtatc      480
taaccagaaa gccacggcta actacgtgcc agcagccgcg gtaatacgta ggtggcaagc      540
gttgtccgga tttattgggc gtaaagcgag cgcaggcggt ttcttaagtc tgatgtgaaa      600
gcccccggct caaccgggga gggtcattgg aaactgggag acttgagtgc agaagaggag      660
agtggaattc catgtgtagc ggtgaaatgc gtagatatat ggaggaacac cagtggcgaa      720
ggcggctctc tggtctgtaa ctgacgctga ggctcgaaag cgtggggagc aaacaggatt      780
agataccctg gtagtccacg ccgtaaacga tgagtgctaa gtgttggagg gtttccgccc      840
ttcagtgctg cagctaacgc attaagcact ccgcctgggg agtacgaccg caaggttgaa      900
```

```
actcaaagga attgacgggg gcccgcacaa gcggtggagc atgtggttta attcgaagca      960
acgcgaagaa ccttaccagg tcttgacatc ctttgaccac tctagagata gagcttcccc     1020
ttcgggggca aagtgacagg tggtgcatgg ttgtcgtcag ctcgtgtcgt gagatgttgg     1080
gttaagtccc gcaacgagcg caacccttat tgttagttgc catcattcag ttgggcactc     1140
tagcaagact gccggtgaca aaccggagga aggtggggat gacgtcaaat catcatgccc     1200
cttatgacct gggctacaca cgtgctacaa tgggaagtac aacgagttgc gaagtcgcga     1260
ggctaagcta atctcttaaa gcttctctca gttcggattg caggctgcaa ctcgcctgca     1320
tgaagccgga atcgctagta atcgcggatc agcacgccgc ggtgaatacg ttcccgggcc     1380
ttgtacacac cgcccgtcac accacgagag tttgtaacac ccgaagtcgg tgaggtaacc     1440
ttttggagcc agccgcctaa ggtgggatag atgattgggg tgaagtcgta acaaggtagc     1500
cgtatcggaa ggtgc                                                      1515
```